US006660812B2

(12) United States Patent
Kuechler et al.

(10) Patent No.: US 6,660,812 B2
(45) Date of Patent: Dec. 9, 2003

(54) PRODUCTION OF OLEFIN DERIVATIVES

(75) Inventors: Keith H. Kuechler, Friendswood, TX (US); Minquan Cheng, Evansville, IN (US); Marc L. DeChellis, Houston, TX (US); David R. Lumgair, Jr., Craddockville, VA (US); Russell D. Sellen, Beaumont, TX (US); Gary F. Janda, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 71 days.

(21) Appl. No.: 09/882,713

(22) Filed: Jun. 15, 2001

(65) Prior Publication Data
US 2003/0045761 A1 Mar. 6, 2003

Related U.S. Application Data
(60) Provisional application No. 60/240,941, filed on Jul. 13, 2000.

(51) Int. Cl.[7] .............................. C08F 2/00; C07C 1/20
(52) U.S. Cl. ........................ 526/68; 526/75; 585/327; 585/407; 585/408; 585/413; 585/518; 585/520; 585/639; 585/903; 570/189; 568/459; 568/579; 568/840; 558/303
(58) Field of Search ...................... 526/68, 75; 585/319, 585/327, 518, 520, 639, 903, 407, 408, 413; 570/189; 558/303; 568/459, 579, 840

(56) References Cited

U.S. PATENT DOCUMENTS

| 3,407,789 | A | | 10/1968 | Hallee et al. ............... 122/356 |
|---|---|---|---|---|
| 3,635,919 | A | | 1/1972 | Goffinet, Jr. ............. 260/80.78 |
| 3,647,682 | A | | 3/1972 | Rabo et al. ................ 208/120 |
| 3,758,403 | A | | 9/1973 | Rosinski et al. ............ 208/120 |
| 3,820,955 | A | | 6/1974 | Woebcke ................. 23/227 R |
| 4,499,327 | A | | 2/1985 | Kaiser ........................ 585/640 |
| 4,814,067 | A | | 3/1989 | Gartside et al. ............ 208/127 |
| 4,828,679 | A | | 5/1989 | Cormier, Jr. et al. ....... 208/120 |
| 4,861,939 | A | | 8/1989 | Debras et al. ............. 585/820 |
| 4,980,053 | A | | 12/1990 | Li et al. ..................... 208/120 |
| 5,541,270 | A | * | 7/1996 | Chinh et al. .................. 526/68 |
| 5,599,955 | A | | 2/1997 | Vora et al. ................... 549/525 |
| 5,981,818 | A | | 11/1999 | Purvis et al. ............... 585/519 |
| 6,121,503 | A | * | 9/2000 | Janssen et al. ............. 585/640 |
| 6,437,208 | B1 | * | 8/2002 | Kuechler et al. ........... 585/640 |

FOREIGN PATENT DOCUMENTS

| WO | WO 92/12184 | 7/1992 | .......... C08F/110/06 |
|---|---|---|---|
| WO | WO 93/24431 | 12/1993 | ........... C07C/11/02 |
| WO | WO 00/21657 | 4/2000 | .............. B01J/8/10 |

* cited by examiner

*Primary Examiner*—Fred Teskin
(74) *Attorney, Agent, or Firm*—Paul T. La Vore

(57) ABSTRACT

Disclosed is a system of making an olefin derivative from a dilute olefin feed. Dilute olefin is sent to an olefin reaction unit to form an olefin derivative product. The olefin derivative product is recovered from the reaction unit while a vent stream is also removed. Olefin is separated from the vent stream, and the olefin is sent to the olefin reaction unit for additional processing.

56 Claims, 2 Drawing Sheets

PRODUCTION OF OLEFIN DERIVATIVES

CROSS REFERENCE TO RELATED APPLICATIONS

This application claims the benefit of provisional application No. 60/240,941 filed Jul. 13, 2000.

FIELD OF THE INVENTION

This invention relates to a system of making an olefin derivative from an olefin feed or its precursor material that has a very low contaminant concentration. More specifically, this invention relates to the making of an olefin derivative by removing a vent stream from an olefin derivative unit, separating olefin from the vent stream, and sending the olefin to an olefin reaction unit.

BACKGROUND OF THE INVENTION

Olefins such as ethylene, propylene, the butenes, and the pentenes are useful in preparing a wide variety of derivative end products. Examples of such end products include polyethylenes, polypropylenes, polyisobutylene and other polymers, alcohols, vinyl chloride monomer, acrylo-nitrile, methyl tertiary butyl ether and tertiary amyl methyl ether and other petrochemicals, and a variety of rubbers such as butyl rubber.

The olefins used in preparing olefin derivative products are typically made by cracking hydrocarbon feedstocks or catalytically converting oxygenate feedstocks. Cracking of hydrocarbon feedstocks can be accomplished catalytically or non-catalytically. Non-catalytic cracking processes are described, for example, in Hallee et al., U.S. Pat. No. 3,407,789; Woebcke, U.S. Pat. No. 3,820,955; DiNicolantonio, U.S. Pat. No. 4,499,055 and Gartside et al., U.S. Pat. No. 4,814,067. Catalytic cracking processes are described, for example, in Cormier, Jr. et al., U.S. Pat. No. 4,828,679; Rabo et al., U.S. Pat. No. 3,647,682; Rosinski et al., U.S. Pat. No. 3,758,403; Gartside et al., U.S. Pat. No. 4,814,067; Li et al., U.S. Pat. No. 4,980,053; and Yongqing et al., U.S. Pat. No. 5,326,465. Catalytic conversion of oxygenate feedstocks to produce olefins are described, for example in, Kaiser, U.S. Pat. No. 4,499,327, Barger, U.S. Pat. No. 5,095,163, and Hoelderich et al., U.S. Pat. No. 4,433,188.

Olefins which are typically used as feedstock in the preparation of derivative end products are supplied at a relatively high purity to the appropriate reaction unit. For example, when the olefin is ethylene and the derivative product is polyethylene, the ethylene is typically supplied at about 99.9 mol %. As another example, when the olefin is propylene and the derivative product is polypropylene, the propylene is typically supplied at about 99.0 wt. %. With advancements in polymerization catalysis, such as single site metallocene catalysts, feedstock requirements have become even more stringent. See, for example, Chang, U.S. Pat. No. 5,238,892; Burkhardt et al., PCT Application No. WO 9212184; and Schreck et al., U.S. Pat. No. 5,280,074. Accordingly, the conventional wisdom in the industry is for olefin derivative producers, particularly the polyethylene and polypropylene producers, to purchase polymer grade ethylene and propylene, and then remove trace contaminants to obtain the desired purity specifications.

Removal of trace contaminants to provide polymer grade ethylene and propylene can, however, be a difficult and expensive task. For example, separating paraffins from olefins having the same carbon number is quite difficult due to the relatively close boiling ranges of the components. When olefin is produced by cracking, particularly by naphtha cracking, additional contaminants are also a problem. For example, Bodart, U.S. Pat. No. 5,432,243, and Debras et al., U.S. Pat. No. 4,861,939, disclose that arsine and carbonyl sulfide (COS) can be problematic in the olefin derivative process unless the contaminants are removed by additional purification equipment. The purification equipment required is generally quite large in scale and quite expensive to operate.

Purvis et al., U.S. Pat. No. 5,981,818, suggest that, contrary to conventional wisdom, it may be possible to produce polyethylene and polypropylene using ethylene and propylene streams which have a higher than convention content of ethane and propane. The so called dilute propylene and ethylene feeds can be used to prepare polypropylene and polyethylene by sending the by-product stream from the polymerization reaction unit back to a cracking unit or a charge gas compressor downstream of the cracking unit.

Recycling by-product streams from the polymerization unit to a cracking unit or a charge gas compressor can bring about additional problems, however. The by-product can contain significant amounts of ethylene and propylene which will either go through the cracker or compressor unchanged, taking capacity from normal feed conversion, or more likely be modified to a different undesirable by-product. In addition, the recycled by-product is likely to contain sufficient amounts of polymerization catalyst to cause the ethylene and propylene to polymerize in either the cracker or the compressor, causing substantial operating problems due to equipment fouling.

SUMMARY OF THE INVENTION

In order to reduce problems associated with contaminant build up in the production of olefin derivative product, this invention provides combining the manufacture of a high quality olefin stream to an olefin reaction unit. Using appropriate recycle of vent gas within the olefin reaction unit allows the high quality olefin stream to be used in the olefin reaction process with reduced risk of equipment fouling and catalyst contamination, while maintaining high product quality.

In one embodiment, the invention provides a method of making an olefin derivative from an olefin stream. The method comprises introducing a dilute olefin stream into an olefin reaction unit; forming an olefin derivative product within the reaction unit; removing the olefin derivative product and a vent stream from the olefin reaction unit; separating olefin from the vent stream; and sending the olefin to the olefin reaction unit. Preferably, the dilute olefin stream comprises at least one $C_2$–$C_5$ olefin stream, more preferably at least 80 wt. % ethylene or 80 wt. % propylene. The vent stream will generally comprise olefin and paraffin.

In another embodiment, the invention is directed to a method of making polyolefin from an oxygenate, which comprises contacting an oxygenate feed with a molecular sieve catalyst to form an olefin-containing product, wherein the olefin-containing product contains less than 10 ppm wt. of a contaminant selected from hydrogen sulfide, carbonyl sulfide, and arsine; separating olefin from the olefin-containing product; contacting the separated olefin with a polyolefin forming catalyst to form a reaction stream comprising polyolefin and a vent gas, wherein the vent gas comprises unreacted olefin; and contacting at least a portion of the unreacted olefin with the polyolefin forming catalyst to form polyolefin. Preferably, the separated olefin is contacted with the polyolefin forming catalyst without having the contaminant previously separated therefrom. In an alternative arrangement, the at least a portion of the unreacted olefin is contacted with the polyolefin forming catalyst without having the contaminant previously separated therefrom.

In another preferred embodiment, the olefin is separated from the olefin-containing product without subsequently separating paraffins from olefins of the same carbon number. It is particularly desirable that ethylene is separated from the olefin-containing product without subsequently separating ethane from the ethylene, and that propylene is separated from the olefin-containing product without subsequently separating propane from the propylene.

In yet another preferred embodiment, the olefin reaction unit includes a polyolefin reactor. The reactor can contain a metallocene catalyst or a Ziegler Natta catalyst.

In another preferred embodiment, the olefin is made from an oxygenate by contacting the oxygenate with a molecular sieve catalyst in which the molecular sieve catalyst is a zeolite or non-zeolite catalyst. Non-zeolite catalysts are preferred. An example of a non-zeolite catalyst includes one which comprises a silicoaluminophosphate molecular sieve. The silicoaluminophosphate molecular sieve is preferably selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof The oxygenate is preferably selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof In still another embodiment, the invention concerns a process for producing polyethylene. The process comprises contacting an oxygenate containing feed with a molecular sieve catalyst to form an ethylene containing product stream; introducing at least a portion of the ethylene containing product stream into a polyethylene reaction unit to form polyethylene; forming polyethylene within the polyethylene reaction unit; removing the polyethylene product and a vent stream from the polyethylene reaction unit; separating ethylene from the vent stream; and sending the ethylene to the polyethylene reaction unit. Preferably, the ethylene sent to the polyethylene reaction unit has a hydrogen sulfide content of not greater than 10 ppm wt., a carbonyl sulfide content of not greater than 10 ppm wt., and an arsine content of not greater than 10 ppm wt. It is also preferred that the ethylene sent to the polyethylene reactor is separated from the ethylene containing product stream without subsequent removal of ethane from ethylene.

In another preferred embodiment, the invention is to a process for producing polypropylene. The process comprises contacting an oxygenate containing feed with a molecular sieve catalyst to form a propylene containing product stream; introducing at least a portion of the propylene containing product stream into a polypropylene reaction unit to form polypropylene; forming polypropylene within the polypropylene reaction unit; removing the polypropylene product and a vent stream from the polypropylene reaction unit; separating propylene from the vent stream; and sending the propylene to the polypropylene reaction unit. Preferably, the propylene sent to the polypropylene reaction unit has a hydrogen sulfide content of not greater than 10 ppm wt., a carbonyl sulfide content of not greater than 10 ppm wt., and an arsine content of not greater than 10 ppm wt. It is also preferred that the propylene sent to the polypropylene reactor is separated from the propylene containing product stream without subsequent removal of propane from propylene.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

Figure 1:
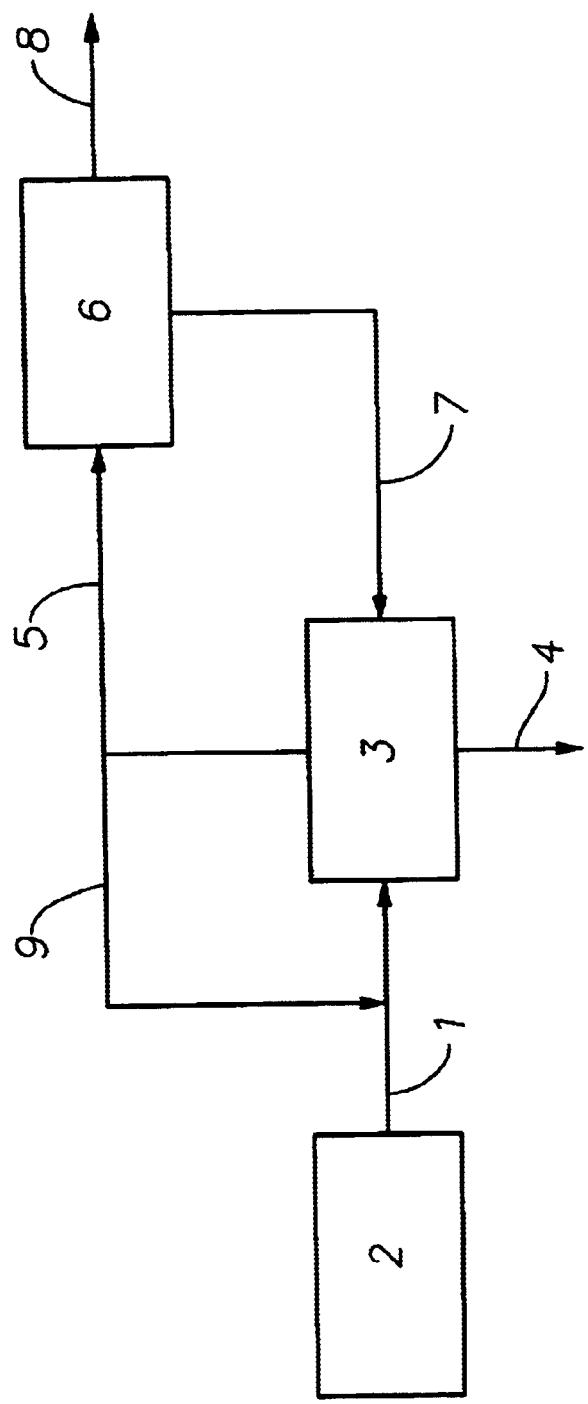
FIG. 1 is an flow diagram of the process of the invention.

This invention provides a system by which an olefin feed stream is converted to an olefin derivative. The system offers a definite advantage in that relatively expensive olefin purification equipment need not be used. This invention is particularly advantageous in that olefin polymerization by-product can be efficiently recycled without significantly adding to the overall load of the reaction and recovery facilities and without significant risk of associated catalyst contaminant problems.

In addition, this invention provides a method for making an olefin derivative from an olefin stream low in contaminants. Desirably, the dilute olefin stream is sent directly to an olefin reaction unit, and a derivative product is formed. However, some processing of the olefin stream can occur before sending to the olefin reaction unit if desired, such as separation of olefins of different carbon number. This would include simple fractionation of such compounds as ethylene from propylene or propylene from butylene.

The olefin stream used as feedstock to make the olefin derivative product is preferably a dilute olefin stream. As used herein, the term dilute olefin refers to an olefin containing stream comprising at least 50 wt. % olefin and less than 100 wt. % olefin. The dilute olefin stream preferably comprises at least 50 wt. % olefin and between 0.1 and 50 wt. % paraffins, more preferably between at least 75 wt. % olefin and between 0.3 and 25 wt. % paraffins, and most preferably between at least 90 wt. % olefin and between 0.5 and 10 wt. % paraffins. Preferably, the olefin comprises at least one or more $C_2$–$C_5$ olefins. Examples of the olefin include ethylene, propylene, and the various forms of the butenes and the pentenes. Ethylene and propylene are particularly preferred olefins.

The term olefin derivative refers to a product made from at least one olefin in the olefin feed stream. Examples of olefin derivatives include polyethylene, polypropylene, polyisobutylene, linear alpha olefins and other polymers, aldehydes, alcohols, acetic acid, acrylic acid, vinyl acetate, vinyl chloride monomer, ethylene dichloride, acrylonitrile, methyl tertiary butyl ether and tertiary amyl methyl ether, ethylbenzene, ethylene oxide, cumene, acrolein, allyl chloride, propylene oxide, and a variety of rubbers such as butyl rubber and ethylene-propylene rubbers, and oligomers of ethylene, propylene or butylenes.

By combining a dilute olefin stream that is low in contaminants with a derivative unit that effectively vents essentially unreactive inert components from the derivative manufacturing process, the overall efficiency of forming derivative product can be significantly increased. The result is that less separation and purification equipment is needed. In large commercial scale processes, this results in significant reduction in equipment costs as well as a significant reduction in operation costs. This reduction in equipment and operation costs can ultimately provide the consumer with a product of the same high quality as conventional systems, but at a significant reduction in cost.

Olefins used in this invention can be obtained from conventional processes, i.e., conventional olefin units. These processes include various cracking processes as well as processes which catalytically convert oxygenate compounds.

The cracking process can be a non-catalytic or a catalytic process. A preferred non-catalytic process is steam cracking. Steam cracking processes are generally carried out in radiant furnace reactors at elevated temperatures for short residence times while maintaining a low reactant partial pressure, relatively high mass velocity, and effecting a low pressure drop through the reaction zone. Any of the furnaces known to those skilled in the art may be employed. Examples of furnaces which can be used in this invention are described in Bowen et al., U.S. Pat. No. 5,151,158; Palchik et al., U.S. Pat. No. 3,274,978; Hallee et al., U.S. Pat. No. 3,407,789; Woebcke, U.S. Pat. No. 3,820,955; Alagy et al., U.S. Pat. No. 4,780,196; DiNicolantonio, U.S. Pat. No. 4,499,055; Martens, U.S. Pat. No. 4,762,958, the descriptions of which are incorporated herein by reference.

The hydrocarbon feed to the steam cracker can be in the liquid or vapor phase or it can comprise a mixed liquid-vapor phase. The most preferred feedstocks for steam cracking are ethane, propane, butane, naphtha, gas oils, gas condensates and mixtures thereof. The hydrocarbon feedstock is preferably in the vapor phase within the steam cracker.

Alternatively, instead of steam cracking other well known cracking processes (both catalytic and non-catalytic) can be employed to produce olefins. Examples of these other cracking processes include thermal regenerative cracking, fluidized bed cracking, fluid catalytic cracking, deep catalytic cracking, and visbreaking.

In the thermal regenerative cracking (TRC) process, inert particulate solids are heated to relatively high temperatures, on the order of from about 1400° F. to about 1600° F. and introduced into a fluidized cracking zone with the hydrocarbon feed. The cracking zone may be upflow (i.e., a riser design), downflow or horizontal in configuration. The hydrocarbon feed is thermally cracked at temperatures ranging from about 1200° F. to about 1600° F. in the cracking zone wherein the heated particulate solids lose heat and are fouled or contaminated with the coke and tars and other heavy cracking products of the hydrocarbon feed. Thereafter, the contaminated solids are separated from the hydrocarbon product gases, stripped and regenerated for re-use in the cracking zone. Regeneration entails burning the contaminants from the particulate solids to heat the solids to a temperature necessary to crack the hydrocarbon feed. See, e.g., Gartside et al., U.S. Pat. No. 4,814,067, Boston, U.S. Pat. No. 2,906,695; Woebcke et al., U.S. Pat. No. 4,318,800; McKinney et al., U.S. Pat. No. 4,061,562; McKinney et al., U.S. Pat. No. 4,097,363 and Gartside et al., U.S. Pat. No. 4,552,645.

In a fluidized catalytic cracking (FCC) process, the process proceeds similarly to thermal regenerative cracking except that the solids are catalytic and the temperatures employed are generally lower. Cracking temperatures are typically on the order of from about 800° F. to about 1300° F. Any conventional fluidized catalytic cracking catalyst can be used. Non-limiting examples of catalyst include Y-type zeolites, USY, REY, RE-USY, faujasite and other synthetic and naturally occurring zeolites and mixtures thereof. See, e.g., Gartside et al., U.S. Pat. No. 4,814,067; Haddad et al., U.S. Pat. No. 4,404,095; Cartmell, U.S. Pat. No. 3,785,782; Castagnos, Jr. et al., U.S. Pat. No. 4,419,221; Cormier, Jr. et al., U.S. Pat. No. 4,828,679; Rabo et al., U.S. Pat. No. 3,647,682; Rosinski et al., U.S. Pat. No. 3,758,403; and Dean et al., U.S. Reissue Pat. No. RE 33,728, the descriptions of which are incorporated herein by reference.

Another cracking process which can be used in accordance with the invention is a deep catalytic cracking (DCC) process. In the DCC process, a preheated hydrocarbon feedstock is cracked over heated solid acidic catalyst in a reactor at temperatures ranging from about 925° F. to about 1350° F., preferably from about 1025° F. to about 1150° F. The weight hourly space velocity of the charge may range from about 0.2 $hr^{-1}$ to about 20 $h^{-1}$, preferably from about 1 $hr^{-1}$ to about 10 $hr^{-1}$. The catalyst-to-oil ratio can vary from about 2 to about 12, preferably from about 5 to about 10. In order to lower the partial pressure of hydrocarbon feed, steam or other gases, such as the dry gas of a catalytic cracking unit, may be added into the reactor during the conversion process.

When steam is used, a weight ratio of steam to hydrocarbon feed is preferably maintained at from about 0.01 to about 0.5:1. The total pressure of the reaction preferably ranges from about 20 psia to about 45 psia, more preferably from about 25 psia to about 35 psia.

After the reaction, the spent catalyst particles can be steam stripped to remove residual hydrocarbons absorbed on the catalyst as is known in the art. The spent catalyst particles with coke deposited thereon are then transferred to a regeneration zone as is also well known to those of ordinary skill in the art.

Regeneration is generally conducted by contacting the catalyst with an oxygen-containing gas at a temperature of from about 1175° F. to about 1350° F. Afterwards the regenerated catalyst is typically recycled to the reaction zone.

Hydrocarbon feedstocks useful in the DCC process can vary in a wide range, and typically are relatively heavy hydrocarbon feedstocks such as those selected from petroleum fractions with different boiling ranges. Non-limiting examples of hydrocarbon feedstocks include naphtha, gas oil, vacuum gas oil, residual oil and mixtures thereof. Crude oil can also be directly used.

Catalysts used in the deep catalytic cracking process step of the present invention are preferably solid, acidic catalysts which comprise one or more active components and a matrix material. The active components preferably include amorphous aluminosilicates or zeolites such as pentasil shape selective molecular sieves, faujasite, rare earth cation exchanged faujasite, chemically treated and/or stabilized faujasite and mixtures thereof. The matrix material preferably includes synthetic inorganic oxides and mineral clays. All of these catalysts are commercially available.

The use of these catalysts at the specified reaction conditions provides for high yields of gaseous olefins, especially propylene and butylenes. For a more detailed description of the DCC process, its catalyst and variations on the DCC process, see, Li et al., U.S. Pat. No. 4,980,053; Shu et al., U.S. Pat. No. 5,232,675; Zhicheng et al., U.S. Pat. No. 5,380,690; Yongqing et al., U.S. Pat. No. 5,326,465 and Yukang et al., U.S. Pat. No. 5,358,918, the descriptions of which are incorporated herein by reference.

In this invention, one or more of the above described cracking processes can be employed. The processes can be configured as separate cracking processes to crack different feedstocks, or used in an integrated process such as described in Rubin et al., U.S. Pat. No. 5,523,502, the description of which is incorporated herein by reference.

In a preferred embodiment, olefins are obtained from the catalytic conversion of oxygenate feed. In this preferred embodiment, contaminant levels are significantly lower than that obtained from other olefin forming processes. This embodiment is particularly advantageous when operated at commercial scale and coupled with commercial scale derivative processes. Such commercial scale olefin forming processes require a catalyst loading of anywhere from 1,000 kg to 700,000 kg, producing anywhere from 600 to 400,000 kg/hr of olefin product. The preferred olefins in such a process are ethylene and propylene. At such large scale operations, even extremely low levels of contaminants can adversely impact derivative product formation, particularly formation of polyethylene and polypropylene. Simplification of contaminant removal at such a large scale can greatly impact the efficiency of the overall process.

The oxygenate feedstock of the preferred embodiment preferably comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include, but are not necessarily limited to, lower straight and branched chain aliphatic alcohols and their unsaturated counterparts. Examples of suitable oxygenate compounds include, but are not limited to, the following: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

Oxygenates can be converted over small pore molecular sieve and zeolite and non-zeolite catalysts having high selectivity to ethylene and/or propylene. Small pore molecular sieves are preferred in this invention. As defined herein, small pore molecular sieves have a pore size of less than about 5.0 Angstroms. Generally, suitable catalysts have a pore size ranging from about 3.5 to about 5.0 angstroms, preferably from about 4.0 to about 5.0 Angstroms, and most preferably from about 4.3 to about 5.0 Angstroms.

Zeolites are complex crystalline aluminosilicates which form a network of $AlO_2^-$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis. The interstitial spaces or channels formed by the crystalline network enable zeolites to be used as molecular sieves in separation processes, as catalyst for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof but also materials which contain suitable replacement atoms for such silicon and aluminum atoms.

Silicoaluminophosphate molecular sieves are preferred embodiments of this invention. These sieves generally comprise a three-dimensional microporous crystal framework structure of $[SiO_2]$, $[AlO_2]$ and $[PO_2]$ tetrahedral units. The way Si is incorporated into the structure can be determined by $^{29}Si$ MAS NMR. See Blackwell and Patton, *J. Phys. Chem.*, 92, 3965 (1988). The desired SAPO molecular sieves will exhibit one or more peaks in the $^{29}Si$ MAS NMR, with a chemical shift $\delta(Si)$ in the range of −88 to −96 ppm and with a combined peak area in that range of at least 20% of the total peak area of all peaks with a chemical shift $\delta(Si)$ in the range of −88 ppm to −115 ppm, where the $\delta(Si)$ chemical shifts refer to external tetramethylsilane (TMS).

It is preferred that the silicoaluminophosphate molecular sieve used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A $Si/Al_2$ ratio of not greater than 0.20 is most preferred.

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size of less than about 5 angstroms, preferably an average pore size ranging from about 3.5 to 5 angstroms, more preferably from 3.5 to 4.2 angstroms. These pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [$MeO_2$] tetrahedral unit. The [$MeO_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AlO_2$ and $PO_2$ tetrahedral units. These as manufactured structures (which contain template prior to calcination) can be represented by empirical chemical composition, on an anhydrous basis, as:

$mR:(M_xAl_yP_z)O_2$ wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, such as by centrifugation or filtration. The product can also be washed, recovered by the same means, and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, dipropylamine, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with theSAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition preferably comprises about 1% to about 99%, more preferably about 5% to about 90%, and most preferably about 10% to about 80%, by weight of molecular sieve. It is also preferred that the catalyst composition have a particle size of from about $20\mu$ to $3,000\mu$, more preferably about $30\mu$ to $200\mu$, most preferably about $50\mu$ to $150\mu$.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

In this invention, a feed containing an oxygenate, and optionally a diluent or a hydrocarbon added separately or mixed with the oxygenate, is contacted with a catalyst containing a SAPO molecular sieve in a reaction zone or volume. The volume in which such contact takes place is herein termed the "reactor," which may be a part of a "reactor apparatus" or "reaction system." Another part of the reaction system may be a "regenerator," which comprises a volume wherein carbonaceous deposits (or coke) on the catalyst resulting from the olefin conversion reaction are removed by contacting the catalyst with regeneration medium.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to, helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof. The preferred diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of reactor product.

In the process of this invention, coked catalyst can be regenerated by contacting the coked catalyst with a regeneration medium to remove all or part of the coke deposits.

This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

Any standard reactor system can be used, including fixed bed, fluid bed or moving bed systems. Preferred reactors are co-current riser reactors and short contact time, countercurrent free-fall reactors in which an oxygenate feedstock can be contacted with a molecular sieve catalyst at a WHSV of at least about 1 $hr^{-1}$ preferably in the range of from about 1 $hr^{-1}$ to 1000 $hr^{-1}$, and most preferably in the range of from about 20 $hr^{-1}$ to 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to 700° C., preferably from about 300° C. to 600° C., more preferably from about 350° C. to 550° C. At the lower end of the temperature range, the formation of the desired olefin products may become markedly slow. At the upper end of the temperature range, the process may not form an optimum amount of product.

The pressure can also vary over a wide range, including autogenous pressures. Effective pressures may be in, but are not necessarily limited to, oxygenate partial pressures at least 1 psia, preferably at least 5 psia. The process is particularly effective at higher oxygenate partial pressures, such as an oxygenate partial pressure of greater than 20 psia. Preferably, the oxygenate partial pressure is at least about 25 psia, more preferably at least about 30 psia. For practical design purposes it is desirable to operate at a methanol partial pressure of not greater than about 500 psia, preferably not greater than about 400 psia, most preferably not greater than about 300 psia.

The conversion of oxygenates to produce light olefins may be carried out in a variety of catalytic reactors. Reactor types include fixed bed reactors, fluid bed reactors, and concurrent riser reactors as described in "Tree Fall Reactor," *Fluidization Engineering*, D. Kunii and O. Levenspiel, Robert E. Krieger Publishing Co. NY, 1977, expressly incorporated herein by reference. Additionally, countercurrent free fall reactors may be used in the conversion process as described in U.S. Pat. No. 4,068,136 and "Riser Reactor," *Fluidization and Fluid-Particle Systems*, pages 48–59, F. A. Zenz and D. F. Othmo, Reinhold Publishing Corp., NY 1960, the detailed descriptions of which are also expressly incorporated herein by reference.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with feed. Typical regeneration temperatures are in the range of 250–700° C., desirably in the range of 350–700° C. Preferably, regeneration is carried out at a temperature range of 450–700° C.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

It may be desirable to cool at least a portion of the regenerated catalyst to a lower temperature before it is sent back to the reactor. A heat exchanger located externally to the regenerator may be used to remove some heat from the catalyst after it has been withdrawn from the regenerator. When the regenerated catalyst is cooled, it is desirable to cool it to a temperature which is from about 200° C. higher to about 200° C. lower than the temperature of the catalyst withdrawn from the reactor. More desirably, it is cooled to a temperature from about 10° C. to 200° C. lower than the temperature of the catalyst withdrawn from the reactor. This cooled catalyst then may be returned to either some portion of the reactor, the regenerator, or both. When the regenerated catalyst from the regenerator is returned to the reactor, it may be returned to the reactor's catalyst disengaging zone, the reaction zone, and/or the inlet zone. Introducing the cooled catalyst into the reactor or regenerator serves to reduce the average temperature in the reactor or regenerator.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

It is preferred that the catalyst within the reactor have an average level of coke effective for selectivity to ethylene and/or propylene. Preferably, the average coke level on the catalyst will be from about 2 wt. % to about 30 wt. %, more preferably from about 2 wt. % to about 20 wt. %. In order to maintain this average level of coke on catalyst, the entire volume of catalyst can be partially regenerated under conditions effective to maintain the desired coke content on catalyst. It is preferred, however, to recycle only a portion of the coked catalyst for feed contact without regenerating. This recycle can be performed either internal or external to the reactor. The portion of coked catalyst to be regenerated is preferably regenerated under conditions effective to obtain a regenerated catalyst having a coke content of less than 2 wt. %, preferably less than 1.5 wt. %, and most preferably less than 1.0 wt. %.

In order to make up for any catalyst loss during the regeneration or reaction process, fresh catalyst can be added. Preferably, the fresh catalyst is added to the regenerated catalyst after it is removed from the regenerator, and then both are added to the reactor. However, the fresh catalyst can be added to the reactor independently of the regenerated catalyst.

The olefin product that is made in the olefin unit is sent to an olefin reaction unit to convert the olefin to an olefin derivative product. Desirably, the olefin product stream is sent directly to the olefin reaction unit with minimal processing for contaminant removal. However, there can be some separation or purification of the olefins in the olefin product stream before sending to the olefin reaction unit if desired.

Purification of olefins traditionally requires removal of low level impurities which interfere with olefin reaction unit performance, particularly polymerization catalyst performance. Low level contaminants generally comprise polar molecules. Examples include oxygenates such as water, alcohols, carboxylic acids, carbon monoxide and carbon dioxide; sulfur compounds such as hydrogen sulfide, carbonyl sulfide and mercaptans; ammonia; arsine; phosphine; and chlorides. Other contaminants can be hydrocarbons such as acetylene, methyl acetylene, propadiene, butadiene, and butyne.

Low level contaminants can be removed by a variety of processes, including hydrogenation reactions to saturate certain hydrocarbons; absorption of certain polar compounds with various materials, such as solid molecular sieves; extraction with various solvents; and fractional distillation. In addition, the desired olefin be separated from a mix of olefins and paraffins having greater and fewer carbon atoms that the desired olefin, as well as from paraffins having the same carbon number. This can be done using conventional fractional distillation techniques, or also using conventional absorbtion, extraction or membrane separations.

In a preferred embodiment of this invention, the olefin product stream is formed from the catalytic conversion of an oxygenate using a molecular sieve catalyst, preferably a silicoaluminophosphate molecular sieve catalyst. This embodiment is particularly desirable when the oxygenate is an alcohol such as methanol or an ether such as dimethyl ether. The resulting olefin product is typically low in contaminants such as hydrogen sulfide, carbonyl sulfide (COS), and arsine. This type of product stream can be processed in an olefin derivative unit with minimal separation and purification. In fact, following recovery of the olefin product directly from the olefin forming unit, removal of hydrogen sulfide, carbonyl sulfide (COS), or arsine is not necessary.

Desirably, the olefin that is sent to the olefin reaction unit has a hydrogen sulfide content of less than 10 parts per million by weight (ppm wt.), preferably less than 5 ppm wt., more preferably less than 1 ppm wt. It is also desirable that the olefin that is sent to the olefin reaction unit have a carbonyl sulfide content of less than 10 parts per million by weight (ppm wt.), preferably less than 5 ppm wt., more preferably less than 1 ppm wt. Likewise, it is desirably that olefin that is sent to the olefin reaction unit have an arsine content of less than 10 parts per million by weight (ppm wt.), preferably less than 5 ppm wt., more preferably less than 1 ppm wt.

Should additional purification of the olefin product stream be needed, purification systems such as that found in *Kirk-Othmer Encyclopedia of Chemical Technology*, 4th edition, Volume 9, John Wiley & Sons, 1996, pg. 894–899, the description of which is incorporated herein by reference, can be used. In addition, purification systems such as that found in *Kirk-Othmer Encyclopedia of Chemical Technology*, 4th edition, Volume 20, John Wiley & Sons, 1996, pg. 249–271, the description of which is also incorporated herein by reference, can be also be used.

In a preferred embodiment of the invention, the olefin stream is sent to the olefin derivative unit without separating olefins from paraffins of like carbon number. Preferably, the olefin product stream is separated and recovered from an oxygenate conversion reaction without subsequent removal of paraffins having the same number of carbon atoms as olefins from the olefin product, and the olefin product has a paraffin-to-olefin weight ratio of less than or equal to about 0.05. A method for providing this type of separation is described in Janasen, U.S. Pat. No. 6,121,503, which is incorporated herein by reference.

In another aspect of this invention, dedicated facilities, such as a fractionation tower for separating ethylene from ethane or for separating propylene from propane, are not required to be employed prior to introducing the dilute olefin stream to the olefins reaction unit making the olefin derivative. In a preferred embodiment, the dilute olefin stream is taken as a result of separating a desired olefin of one carbon number away from olefins and paraffins of a different carbon number, most preferably as the overhead stream of a fractionation tower performing such a service. One skilled in the art will appreciate that some minor separation of olefins from paraffins of like carbon number may occur in the process of separating an olefin of one carbon number from an olefin of a different carbon number.

Alternative embodiments incorporate the use of a dilute olefin stream obtained by employing equipment to separate desired olefins from paraffins of like carbon number that are substantially reduced in size and duty relative to those conventionally employed. For example, in a conventional steam cracker utilizing a fractionation tower to produce chemical grade propylene, feeds to the fractionation tower on the order of about 60 wt. % propylene and about 40 wt. % propane are separated to provide an overhead olefin product stream of greater than or equal to 95 wt. % propylene. In a preferred embodiment of this invention, a dilute olefin stream of less than 95 wt. % propylene can be obtained by using substantially fewer trays in the fractionation tower with a substantially lower reflux ratio, saving both investment and operating costs on the fractionation tower. Alternatively, an existing fractionation tower of a given size and duty to make an olefin stream of greater than or equal to 95 wt. % propylene can have its capacity increased if it is allowed to produce a dilute olefin stream of less than 95 wt. % propylene.

Another desirable embodiment of an olefin purification system eliminates the need for cryogenic fractional distillation and other special separation equipment operating at temperatures below −55° F. In this embodiment, a secondary ethylene rich product stream is produced at a rate and composition suitable for subsequent generation of a primary ethylene rich product potentially containing substantially no components having a boiling point at least as low as ethylene. Further description of this embodiment is provided in Kuechler, et. al., U.S. Pat. No. 5,960,643, which is incorporated herein by reference.

In another aspect of the invention, a dilute olefin stream contains substantial quantities of two or more olefins of contiguous carbon number, e.g., C2 and $C_3$ or $C_3$ and $C_4$. Such a stream can be provided from the overhead of a fractionation tower which separates $C_3^-$ components from $C_4^+$ components, which components can be provided, for example, from a feed generated as the bottoms of another fractionation tower separating $C_1^-$ components from $C_2^+$ components, rather than feeding to the olefin reaction unit two independent streams of $C_2$ and $C_3$ olefins. In this manner, an entire fractionation column can potentially be eliminated over conventional methods.

The olefins stream provided by the olefins unit can be sent to the appropriate olefin reaction unit in order to make the desired olefin derivative product. Any conventional olefin derivative reaction unit can be used. The feed stream to the olefin reaction unit is preferably low in contaminants which would adversely affect the reaction catalyst or adversely impact the quality of the derivative product, particularly hydrogen sulfide, COS and arsine. In another preferred embodiment, a dilute olefin stream can be used as the olefin feed stream with proper venting of the product stream. This means that less processing of the feed stream is necessary, since a significant amount of inert compounds can be tolerated in the olefin reaction unit. Preferably, the olefin reaction unit is a polyethylene or polypropylene reactor.

In a preferred embodiment, a dilute ethylene stream is used as feedstock for a polyethylene polymerization process. The dilute ethylene feedstock for use in the polyethylene polymerization process preferably contains at least about 80 weight percent ethylene, more preferably at least about 85 weight percent, most preferably at least about 90 weight percent.

The ethylene can be polymerized into polyethylene either by gas phase polymerization methods or by solution polymerization methods. Preferably the ethylene concentration of the feedstock is above about 80 wt. %, and below about 100 wt. %, preferably below about 99 wt. %. At an ethylene concentration of at least about 90 wt. %, and below about 99 wt. %, the gas phase polymerization methods may be preferred.

Both the gas phase and solution polymerization methods are well known to those of ordinary skill in the art and any of these known methods may be employed in the practice of the present invention. These processes are typically offered in the industry by companies including but not limited to Exxon Mobil Corporation, Dow Chemical Company, Union Carbide Corporation, British Petroleum Company, Novacor, Mitsui, and DSM. Typical operating parameters include pressures ranging from about 300 psig to about 3000 psig and temperatures ranging from about 200° F. to about 600° F. over catalysts such as those of the Ziegler-Natta (Z/N) family and the "single site" metallocene family. See, e.g., Benham et al., U.S. Pat. No. 5,364,915; Chang, U.S. Pat. No. 5,238,892; Cann et al., U.S. Pat. No. 5,102,841; Beran et al., U.S. Pat. No. 4,508,842; Geerts et al., European Patent No. 0 612 753; Wagner et al., European Patent No. 0 012 147; Karol, Frederick J., "The Polyethylene revolution," Chemtech, April 1983, pp. 222–28; "New route to low-density polyethylene," Chemical Engineering, Dec. 3, 1979, pp. 80–85; Hatch & Matar, "From Hydrocarbons to Petrochemicals," (hereinafter "HATCH & MATAR") pp. 172–176, the descriptions of each being incorporated herein by reference.

Dilute ethylene can also be used as feedstock for other derivative processes, particularly derivative processes which have high once through conversion of the ethylene. Processes such as these include, but are not limited to, processes for the production of ethylene dichloride, alpha olefins, ethyl benzene, styrene and acetaldehyde are also contemplated as within the scope of this invention. The details of these processes are known in the art. See, for example, HATCH & MATAR, pp. 97–98; Kurtz et al., U.S. Pat. No. 3,839,475; Severino, U.S. Pat. No. 4,172,099; Geigert et al., U.S. Pat. No. 4,426,449; Leuck et al., U.S. Pat. No. 4,554,392; HATCH & MATAR, pp. 137–138; Smith, Jr. et al., U.S. Pat. No. 5,243,115; Lee et al., U.S. Pat. No. 5,243,116; HATCH & MATAR, pp. 138–140; Hong et al., U.S. Pat. No. 4,263,212; HATCH & MATAR, pp. 99–101; Nishimura et al., U.S. Pat. No. 4,521,631; and Showa Denko, JP 51-146410, the descriptions of each being incorporated herein by reference.

In another preferred embodiment, a dilute propylene stream is used as feedstock for a polypropylene polymerization process. The dilute propylene stream desirably contains at least about 80 wt. % propylene, preferably at least about 85 wt. % propylene, more preferably at least about 90 wt. % propylene, and most preferably at least about 95 wt. % propylene. In another embodiment, the dilute propylene stream desirably contains at least about 99 wt. % propylene.

The propylene is desirably polymerized into a polypropylene homopolymer. This can be accomplished by bulk phase polymerization methods or by gas phase polymerization methods. At propylene feedstock concentrations of at least about 95 wt. %, the bulk phase polymerization method is preferred.

Conventional bulk phase or gas phase polypropylene polymerization methods can be used in this invention. These processes are operated at commercial scale by such companies as Union Carbide Corporation, Amoco Oil Company and Himont now (Montell). Typical operating parameters include pressures ranging from about 150 psig to about 1000 psig and temperatures ranging from about 200° F. to about 600° F. Catalysts such as those of the Ziegler-Natta family (Z/N) and the "single site" metallocene family can be used. These catalysts are described in further detail by Schreck et al., U.S. Pat. No. 5,280,074; Ardell et al., U.S. Pat. No. 4,956,426; and Selman et al., U.S. Pat. No. 4,287,091, and HATCH & MATAR, pp. 176–79, the descriptions being incorporated herein by reference.

Following the polypropylene homopolymer polymerization process, the polypropylene homopolymer can be copolymerized with ethylene, i.e., 2 to 15 weight percent ethylene, in an impact reactor. The impact reactor desirably operates in the gas phase, and at a pressure ranging from about 150 psig to about 400 psig, and a temperature ranging from about 200° F. to about 400° F. over catalysts such as those of the Ziegler-Natta (Z/N) family as well as the "single site" metallocene family.

Dilute propylene can also be used in other derivative processes, particularly processes which achieve high once through conversion of the propylene. Non-limiting examples of such processes include processes for making acrylonitrile, cumene, propylene oxide, isopropanol, acrolein, and allyl chloride. The details-of these processes are known in the art. See, for example, HATCH & MATAR, pp. 106–119 and 140; Shaw et al., U.S. Pat. No. 5,288,473; Suresh et al., U.S. Pat. No. 5,258,543; Paparizos et al., U.S. Pat. No. 5,235,088; Binns et al., U.S. Pat. No. 3,635,803; Preston et al., U.S. Pat. No. 5,349,072; Keating et al., U.S. Pat. No. 5,274,138; Etzkorn et al., U.S. Pat. No. 5,198,578; Etzkorn et al., U.S. Pat. No. 5,183,936; Honda et al., U.S. Pat. No. 5,144,090;

Caillod et al., U.S. Pat. No. 5,300,707; Dianis, U.S. Pat. No. 5,262,575; Riegel et al., U.S. Pat. No. 4,558,167; Guesinov et al., U.S. Pat. No. 4,244,892; Bach et al., U.S. Pat. No. 3,855,321; Riegel et al., United Kingdom Patent No. GB 2,039,905; Smith, Jr., U.S. Pat. No. 5,262,576; Lee et al., U.S. Pat. No. 5,243,116; Johnson, U.S. Pat. No. 4,463,207; Cavani et al., U.S. Pat. No. 4,992,608; Ward, U.S. Pat. No. 4,008,290; Johnson, U.S. Pat. No. 4,524,229; Sartorio et al., U.S. Pat. No. 4,343,957; and Smith, Jr. et al., U.S. Pat. No. 5,055,627, the descriptions of each being incorporated herein by reference.

In general, dilute olefin streams comprise a significant portion of paraffins. These compounds are not typically harmful to the various derivative processes. However, on certain derivative units, consumption of the olefin in the feed to the derivative unit reactor is not complete, and a recycle of olefins in the reactor effluent is desired. In this event, paraffins may build up in the recycle loop and reduce the concentration of reactive olefins to unacceptable levels.

One feature of this invention is the removal of a vent stream from the olefin reaction unit. As shown in FIG. 1, a dilute olefin stream 1 is sent from an olefins unit 2 to an olefins reaction unit 3. A derivative product 4 is removed from the olefins reaction unit, along with a vent stream 5.

The vent stream 5 contains at least a portion the effluent of the reactor or reactors in the olefin reaction unit. Thus the vent stream comprises unreacted olefin feedstocks, and inerts including paraffins introduced to the olefin reaction unit in the dilute olefin stream. The vent stream 5 is removed from the olefin reaction unit to maintain the inerts balance in the olefin reaction unit reactor system, that is, to keep the reactant olefins at the desired concentration in the feed and effluent of the reactor system.

In a preferred embodiment, a portion of the vent stream is recycled via a line 9 back to the reaction unit 3. In particular, in a vapor phase polyethylene reactor, it is desirable that a portion of the vent stream be recycled to maintain from 2% to 5% olefin conversion per pass to control heat release within the reaction unit 3.

The vent stream 5 desirably comprises olefin, and it can include paraffin Preferably the vent stream 5 comprises 10 to 95 wt. % olefin, more preferably 20 to 90 wt. % olefin. The olefin composition can include ethylene, propylene, butenes, pentenes, and combinations thereof. When the reaction unit 3 is a polyethylene or polypropylene reaction unit, the olefin composition can also include comonomers which are desirable for incorporating into the polymer product. Examples of such compounds include one or more linear alpha olefins having 4–12 carbons. Representative of such olefins are butene-1, hexene-1, octene-1, decene-1, and dodecene-1. The balance of the vent stream 5 can include other feedstocks, by-products, and inerts fed to the olefin generation unit. Such compounds include, for example, hydrogen, methane, ethane, nitrogen, propane, butane, iso-butane, pentane, various iso-pentane isomers, hexane, and various isohexane isomers.

It is desirable to remove at least a portion of the non-olefin compounds from the vent stream 5 using an olefin separation unit 6. After a desired portion of the non-olefin compounds have been removed as a purge stream 8, the remainder of the stream can be recycled back to the olefin reaction unit 3 as an olefin recycle stream 7. If the non-olefin compounds are not removed before recycling back to the olefin reaction unit 3, the concentration of the compounds will likely become to high for the recycle to be effective. This is because the non-olefin compounds are largely non-reactive and, as a result, will tend to build to an unacceptable level within the reaction unit 3. This also means that, in general, the larger the content of inerts introduced to the olefin reaction unit, including paraffins introduced with the dilute olefin stream of the present invention, the larger the vent stream 5 will be.

Once the total amount of paraffins and other inerts to the olefin reaction unit 3 is set, the rate of vent stream 5 is determined by the desired extent of removal of the non-olefin compounds through olefin purge stream 8. In a preferred embodiment, at least 50 wt. % of the total of inerts and paraffins in stream 5 are removed through purge stream 8, more preferably at least 75 wt. %, and most preferably at least 90 wt. %.

Thus, according to this invention, the vent stream 5 is sent to an olefin separation unit 6, where an olefin stream 7 is recovered and returned to the reactors in olefin reaction unit 3. Examples of olefin separation unit 6 include fractional distillation equipment, including dephlegmators, and absorbtion, extractive or membrane separation equipment, and combinations thereof. One particular example is disclosed in Mehrta, U.S. Pat. No. 5,019,143, the description of which is incorporated herein by reference.

In a preferred embodiment, the olefin separation unit 6 is an absorbtive distillation unit which uses lean physical solvents comprised substantially of olefins. Preferably the solvents include linear alpha olefins having 4–12 carbons. More preferably, the linear alpha olefins are to be used as a comonomer in the manufacture of polyolefins. Examples of such olefins include butene-1, hexene-1, octene-1, decene-1 and dodecene-1. Most preferably, the lean oil will be incorporated into the polyolefin product. Another desirable lean physical solvent is iso-pentane.

In another preferred embodiment of this invention, the olefin separation unit 6 is a fractional distillation unit. Preferably, the fractional distillation unit is operated without the use of a lean physical solvent. It is also preferred that the olefin separation unit 6 include refrigeration components which operate at below 50° F. Additional separation components can include condensers and dephlegmators. The olefin separation unit 6 can also be used to purify olefins from the olefins unit 2 if desired.

Preferably the olefin recycle stream 7 comprises at least 50 wt. % of the olefins contained in the vent stream 5, more preferably at least 75 wt. %, and most preferably at least 90%. The balance of the recovered olefin stream 7 may comprise paraffins and other materials found in the vent stream 5. It is also preferred that the olefin recycle stream 7 comprise less than 50 wt. % saturates, more preferably less than 20 wt. %, and most preferably less than 5 wt. % saturates.

A paraffin purge stream 8 will also be obtained from vent recovery unit 6. This stream will comprise at least 50 wt. %, preferably at least 75 wt. %, and more preferably at least 90 wt. % of the paraffins contained in the vent stream 5 sent to the olefin reaction unit. The balance of saturate purge stream 8 may comprise desired olefin and other materials found in vent stream 5, as noted above. Preferably, saturate purge stream 8 will comprise no more than 50 wt. %, more preferably no more than 20 wt. %, and most preferably no more than 5% of desired olefins.

The paraffin purge stream 8 can comprise a very high proportion of the paraffin entering the olefin reaction unit 3, with the balance of those paraffins leaving the olefin reaction unit as losses with the polyolefin product 4 or other inert material purges, not shown in FIG. 1 but described in the Examples below. Thus the rate of paraffin purge stream 8 will be essentially the rate of paraffins in dilute olefin stream 1 divided by the proportion of paraffin in paraffin purge stream 8.

Figure 2:
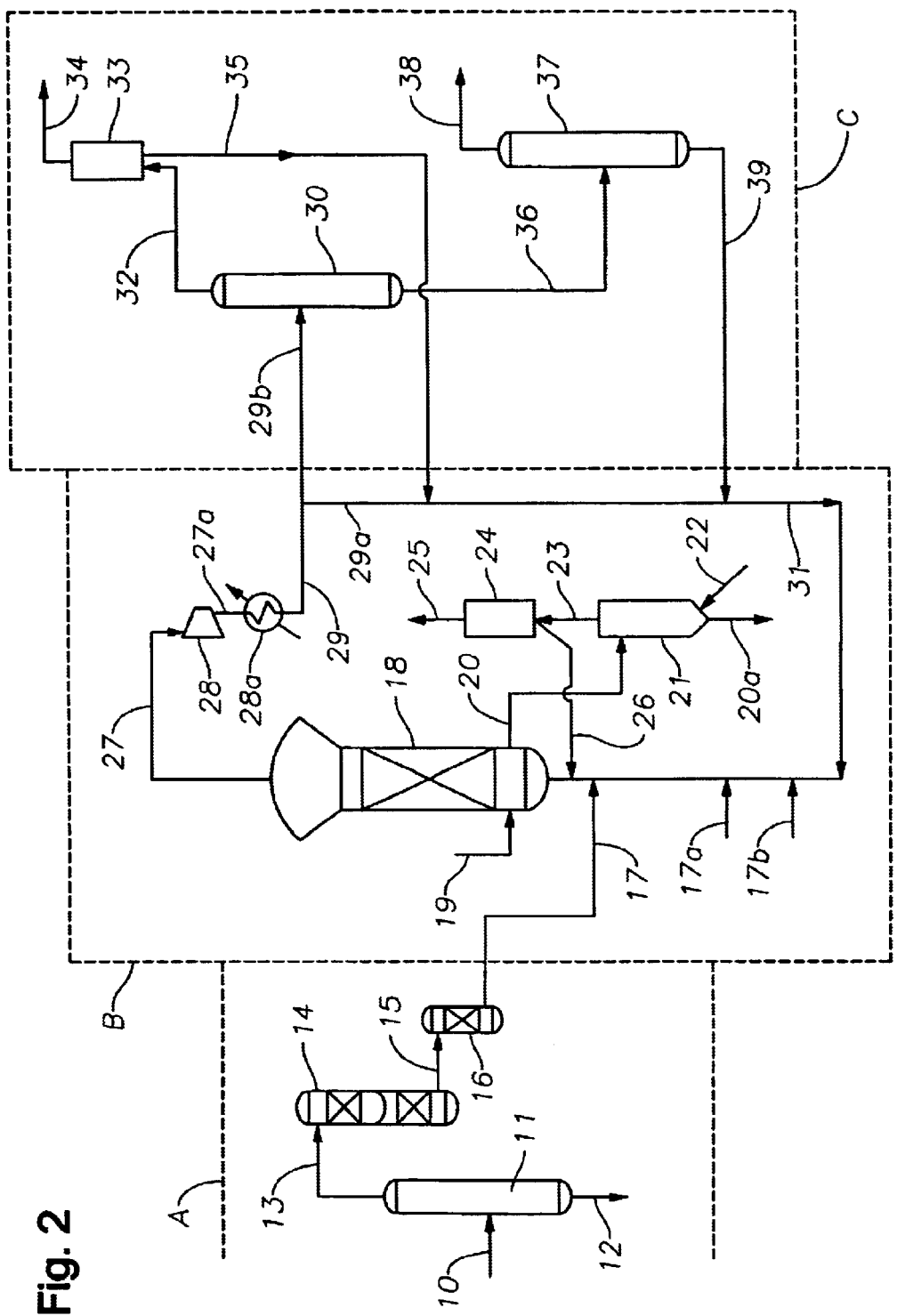
FIG. 2 is a flow diagram of a desired embodiment of the invention.

A preferred embodiment of this invention is shown in FIG. 2, in which olefin feed stream 10, within olefin unit A, comprises a substantial quantity of ethylene and propylene. The olefin feed stream 10 is sent to a deethanizer fractionation tower 11, which separates the olefin feed into a deethanizer bottoms stream 12 and a deethanizer overhead stream 13. The deethanizer bottoms stream 12 is rich in propylene, and the deethanizer overhead stream 13 is rich in ethylene. The deethanizer overhead stream 13 is sent to an acetylene converter 14 for converting acetylene compounds to olefin compounds. Acetylene converter product 15 is sent to a molecular sieve dryer 16 to remove water that may have been formed in the acetylene conversion reaction, providing a dry dilute olefin stream 17. It is desirably that the dry dilute olefin stream be substantially free of water, as even low levels of water may harm some of the catalysts utilized in olefin reaction units.

Dry dilute olefin stream 17 is passed into an olefin reaction unit B, ultimately into an olefin derivative reactor 18. Preferably the olefin derivative reactor 18 is a polyolefin reactor. In this example, the polyolefin reactor 18 is a vapor phase polyethylene reactor of the type offered by Union Carbide Corporation in its Unipol® process. Catalyst, co-catalyst and other materials needed to enable the proper function of the reactor 18 are introduced via line 19.

In a preferred embodiment, a co-reactant stream 17a (or streams) is also added to the polyolefin reactor 18. The co-reactor stream can include one or more co-monomers. Examples include linear alpha-olefins with carbon numbers between four and twelve, preferably butene-1, hexene-1, octene-1, decene-1 and dodecene-1; and vinyl acetate. Preferably, the co-monomer is butene-1. Co-reactant stream 17a can also include hydrogen, which can be used to terminate the polymerization reaction and control molecular weight distribution of the product polymer. A heat control agent 17b can also be fed to the reactor. An example of a heat control agent is iso-pentane.

Polyethylene product 20, which contains unreacted olefins and other compounds as well as polyethylene product, is sent to a light hydrocarbon flash tank 21, from which a light hydrocarbon stream 23 is separated from a polyethylene product stream 20a. In one embodiment, a stripping stream 22 such as nitrogen, preferably methane and more preferably ethane, can be supplied to the light hydrocarbon flash tank 21 to facilitate the separation. Stripped polyethylene product 20a is removed from the light hydrocarbon flash tank 21. The stripped product can be subjected to further processing, including but not limited to secondary light hydrocarbon stripping, compounding with various polymer performance additives, pelletization and storage.

Light hydrocarbon stream 23 is sent to a co-reactant recovery unit 24. Preferably, the co-reactant recovery unit 24 includes a refrigerated flash or a dephlegmator, operated at conditions effective to produce a recovered co-reactant stream 26. The co-reactant 26 will comprise compounds having a higher boiling point than that contained in the dilute olefin. Recovered co-reactant stream 26 is returned to the reactor 18 for further incorporation into the polymer product. Also produced from co-reactant recovery unit 24 is an inert purge stream 25. The inert purge stream 25 comprises inerts as well as co-reactants having a boiling point above the dilute olefin. The co-reactants can include hydrogen, nitrogen, olefin, and co-reactant. The inert purge stream 25 is generally used as a fuel gas to provide heat to other equipment in the olefin or olefin reaction unit, or it can be disposed of by flaring.

When the olefin derivative reactor 18 is a vapor phase polyethylene reactor, it is desirable that a total of only about 2 to 5 wt. % of the olefin and co-reactant present in the feed to the reactor 18 is converted to polymer product. An effluent stream 27, which contains a large amount of unreacted olefin, as well as other compounds present in the reactor 18, exits the reactor 18.

The effluent stream 27 is sent to a compressor 28, which generates a compressed stream 27a at an increased pressure over that of vapor effluent stream 27 to allow for subsequent processing. The compressed stream 27a is sent to a heat exchanger 28a to remove the heat of compression and the heat of reaction generated in creating the polyethylene in reactor 18. The removal of heat condenses at least a portion of iso-pentane which can be present in the compressed stream 27a. This results in a cooled compressed stream 29.

The cooled compressed stream 29 is split into two streams, a compressed recycle 29a and a vent stream 29b, which corresponds to vent stream 5 in FIG. 1. The compressed recycle stream 29a is returned to reactor 18 for further conversion of ethylene to polyethylene. Vent stream 29b is sent to an olefins separation unit C.

In the olefins separation unit C, the vent stream 29b is sent to a deethylenizer fractionation tower 30, which separates ethylene and lighter components as a deethylenizer overhead product 32. The deethylenizer product 32 is sent to a dephlegmator 33, to separate ethylene and heavier components in a recovered olefins stream 35 from an inert purge stream 34. The inert purge stream 34 comprises compounds having a lower boiling point than ethylene. Such compounds include hydrogen, methane and nitrogen.

Since the separation of ethylene from methane and hydrogen is difficult, there can be a significant quantity of ethylene in the purge stream 34. In a preferred embodiment, the purge stream 34 is further fractionated for recovery of the ethylene. The ethylene is then sent to the reactor 18. In another preferred embodiment, the purge stream 34 is utilized in a second olefin reaction unit, preferably in the manufacture of aldehydes and alcohols. A preferred method for manufacturing aldehydes and alcohols is described in Kuechler, U.S. Pat. No. 5,960,643, the detailed description of which is incorporated herein by reference.

The deethylenizer fractionation tower 30 also produces a deethylenizer bottoms product 36. The bottoms product 36 comprises ethane and higher boiling components. The higher boiling components can include butene-1 and iso-pentane. The bottoms product 36 contains little if any ethylene and lighter components.

The bottoms product 36 is sent to a deethanizer fractionation tower 37. The deethanizer fractionation tower 37 separates the ethane and lighter components from the components having higher boiling point range than the ethane containing fraction. The ethane and lighter components are removed from the deethanizer fraction tower 37 as a purge stream 38, which corresponds to the purge stream 8 in FIG. 1.

In a preferred embodiment, the purge stream 38 is sent as feed to an olefin unit. In another preferred embodiment, the purge stream 38 is flashed to reduce its temperature, and then utilized to provide refrigeration.

The components having a higher boiling range than the ethane containing fraction are removed from the deethanizer fraction tower 37 as a recovered olefins stream 39. The recovered olefins stream 39 is rich in olefin, primarily comprising butene-1. Isopentane can also be included. The recovered olefins stream 39 is returned to reactor 18 for further conversion of olefin to polyethylene and provide the reactor cooling effect of the isopentane.

In operation, it is desirable that the rate of stream 29b will be the rate of paraffins to the reactor in the dilute olefin stream 17 less the rate of paraffins in the purge stream 25, divided by the proportion of paraffin in the effluent stream 27. The balance of the effluent stream 27 is returned to the reactor 18 as a compressed recycle stream 31.

In an alternative embodiment, the vent stream 29b (or 5) can be sent to a bulk separation device to separate any entrained liquids or solids from the vapor to the olefin separation unit. Such devices include packed towers or vessels filled with such internals as crinkle wire mesh screens. Alternatively, a liquid material, preferably fresh iso-pentane or a co-reactant such as butene-1 or hexene-1, or condensed co-reactant and diluent such as the recovered olefins stream 39, can be sent to a packed or trayed tower to wash the vapor and further prevent entrained solids from entering the olefin separation unit.

One skilled in the art can readily appreciate the many variations in equipment and configurations that can be employed in the current invention without varying from the scope of the current invention. For example, the vent stream 29 can first be introduced to a tower which separates heavy components such as butene-1 and iso-pentane from ethane and lighter components. The heavy components are returned to the reactor for further reaction. The ethane and lighter components can be introduced to a deethylenizer tower, with the overhead of the deethylenizer tower sent to a dephlegmator. This means that the deethanizer fraction tower 37 can come before the deethylenizer fractionation tower 30.

Having now fully described this invention, it will be appreciated by those skilled in the art that the invention can be performed within a wide range of parameters within what is claimed, without departing from the spirit and scope of the invention.

What is claimed is:

1. A method of making an olefin derivative from an olefin stream, comprising:
    introducing a dilute olefin stream comprising ethylene and/or propylene into an olefin reaction unit;
    forming an olefin derivative product within the reaction unit;
    removing the olefin derivative product and a vent stream from the olefin reaction unit;
    separating the vent stream into an ethylene and/or propylene containing stream and a purge stream;
    sending the ethylene and/or propylene containing stream to the olefin reaction unit; and
    purging the purge stream from the reaction unit.

2. The method of claim 1, wherein the dilute olefin stream comprises at least 50 wt. % ethylene and/or propylene and less than 100 wt. % ethylene and/or propylene.

3. The method of claim 1, wherein the dilute olefin stream comprises less than 99 wt. % ethylene.

4. The method of claim 1, wherein the dilute olefin stream comprises less than 99 wt. % propylene.

5. The method of claim 1, wherein the dilute olefin stream comprises at least 80 wt. % ethylene.

6. The method of claim 1, wherein the dilute olefin stream comprises at least 80 wt. % propylene.

7. The method of claim 1, wherein the dilute olefin stream comprises 85–95 wt. % ethylene.

8. The method of claim 1, wherein the dilute olefin stream comprises 85–95 wt. % propylene.

9. The method of claim 1, wherein the olefin reaction unit is a process unit selected from the group consisting of a polyethylene unit, a polypropylene unit, an acrylonitrile unit, a cumene unit, a propylene oxide unit, an isopropanol unit, an acrolein unit, and an allyl chloride unit.

10. The method of claim 1, wherein the olefin derivative product comprises polyethylene, polypropylene, acrylonitrile, cumene, propylene oxide, isopropanol, acrolein, or allyl chloride.

11. The method of claim 1, wherein the vent stream comprises paraffin.

12. The method of claim 1, wherein the dilute olefin stream comprises less than 10 ppm wt. of a contaminant selected from hydrogen sulfide, carbonyl sulfide, and arsine.

13. A method of making polyolefin from an oxygenate, comprising:
    contacting an oxygenate feed with a molecular sieve catalyst to form an olefin-containing product, wherein the olefin-containing product contains ethylene and/or propylene and less than 10 ppm wt. of a contaminant selected from hydrogen sulfide, carbonyl sulfide, and arsine;
    separating ethylene and/or propylene from the olefin-containing product;
    contacting the separated olefin with a polyolefin forming catalyst to form a reaction stream comprising polyolefin and a vent gas, wherein the vent gas comprises unreacted ethylene and/or propylene;
    separating the vent gas into an ethylene and/or propylene containing stream and a purge stream;
    purging the purge stream; and
    contacting at least a portion of the unreacted olefin with the polyolefin forming catalyst to form polyolefin.

14. The method of claim 13, wherein the ethylene and/or propylene containing stream contains at least 50 wt. % ethylene and/or propylene.

15. The method of claim 14, wherein the ethylene and/or propylene containing stream comprises at least 50 wt. % ethylene.

16. The method of claim 14, wherein the ethylene and/or propylene containing stream comprises at least 50 wt. % propylene.

17. The method of claim 13, wherein the ethylene and/or propylene containing stream contains at least 50 wt. % ethylene and/or propylene and between 0.1 and 50 wt. % paraffins.

18. The method of claim 17, wherein the ethylene and/or propylene containing stream contains at least 75 wt. % ethylene and/or propylene and between 0.3 and 25 wt. % paraffins.

19. The method of claim 18, wherein the ethylene and/or propylene containing stream contains at least 90 wt. % ethylene and/or propylene and between 0.5 and 10 wt. % paraffins.

20. The method of claim 13, wherein the olefin-containing product has a hydrogen sulfide content of not greater than 5 ppm wt., a carbonyl sulfide content of not greater than 5 ppm wt., and an arsine content of not greater than 5 ppm wt.

21. The method of claim 13, wherein ethylene and/or propylene is separated from the olefin-containing product without subsequently separating paraffins from ethylene and/or propylene having the same carbon number.

22. The method of claim 13, wherein the polyolefin comprises polyethylene.

23. The method of claim 13, wherein the polyolefin comprises polypropylene.

24. The method of claim 13, wherein the polyolefin forming catalyst contains a metallocene catalyst.

25. The method of claim 13, wherein the polyolefin forming catalyst contains a Ziegler Natta catalyst.

26. The method of claim 13, wherein the molecular sieve catalyst is a zeolite catalyst.

27. The method of claim 26, wherein the molecular sieve catalyst is a non-zeolite catalyst.

28. The method of claim 26, wherein the non-zeolite catalyst comprises a silicoaluminophosphate molecular sieve.

29. The method of claim 28, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof.

30. The method of claim 29, wherein the silicoaluminophosphate molecular sieve is selected from the group consisting of SAPO-18, SAPO-34, SAPO-35, SAPO-44, SAPO-47, the metal containing forms thereof, and mixtures thereof.

31. The method of claim 13, wherein the oxygenate is selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof.

32. The method of claim 31, wherein the oxygenate is selected from the group consisting of methanol, dimethyl ether, and mixtures thereof.

33. A process for producing polyethylene, comprising:
    contacting an oxygenate containing feed with a molecular sieve catalyst to form an ethylene containing product stream;
    introducing at least a portion of the ethylene containing product stream into a polyethylene reaction unit to form polyethylene;
    forming polyethylene within the polyethylene reaction unit;
    removing the polyethylene product and a vent stream from the polyethylene reaction unit;
    separating ethylene from the vent stream; and
    sending the ethylene to the polyethylene reaction unit.

34. The method of claim 33, wherein the oxygenate is selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof.

35. The method of claim 34, wherein the oxygenate is selected from the group consisting of methanol, dimethyl ether, and mixtures thereof.

36. The method of claim 33, wherein the molecular sieve catalyst is a silicoaluminophosphate molecular sieve catalyst.

37. The method of claim 36, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof.

38. The method of claim 37, wherein the silicoaluminophosphate molecular sieve is selected from the group consisting of SAPO-18, SAPO-34, SAPO-35, SAPO-44, SAPO-47, the metal containing forms thereof, and mixtures thereof.

39. The method of claim 33, wherein the portion of the ethylene containing product stream introduced to the polyethylene reaction unit comprises at least 50 wt. % ethylene and between 0.1 and 50 wt. % ethane.

40. The method of claim 39, wherein the portion of the ethylene containing product stream introduced to the polyethylene reaction unit comprises at least 75 wt. % ethylene and between 0.3 and 25 wt. % ethane.

41. The method of claim 40, wherein the portion of the ethylene containing product stream introduced to the polyethylene reaction unit comprises at least 90 wt. % ethylene and between 0.5 and 10 wt. % ethane.

42. The method of claim 33, wherein the ethylene introduced into the polyethylene reaction unit has a hydrogen sulfide content of not greater than 10 ppm wt., a carbonyl sulfide content of not greater than 10 ppm wt., and an arsine content of not greater than 10 ppm wt.

43. The method of claim 33, wherein the ethylene introduced into the polyethylene reactor is separated from the ethylene containing product stream without subsequent removal of ethane from ethylene.

44. The method of claim 33, wherein the vent stream comprises ethylene and ethane.

45. A process for producing polypropylene, comprising:
    contacting an oxygenate containing feed with a molecular sieve catalyst to form a propylene containing product stream;
    introducing at least a portion of the propylene containing product stream into a polypropylene reaction unit to form polypropylene;
    forming polypropylene within the polypropylene reaction unit;
    removing the polypropylene product and a vent stream from the polypropylene reaction unit;
    separating propylene from the vent stream; and
    sending the propylene to the polypropylene reaction unit.

46. The method of claim 45, wherein the oxygenate is selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof.

47. The method of claim 46, wherein the oxygenate is selected from the group consisting of methanol, dimethyl ether, and mixtures thereof.

48. The method of claim 45, wherein the molecular sieve catalyst is a silicoaluminophosphate molecular sieve catalyst.

49. The method of claim 48, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof.

50. The method of claim 49, wherein the silicoaluminophosphate molecular sieve is selected from the group consisting of SAPO-18, SAPO-34, SAPO-35, SAPO-44, SAPO-47, the metal containing forms thereof, and mixtures thereof.

51. The method of claim 45, wherein the portion of the propylene containing product stream introduced to the polypropylene reaction unit comprises at least 50 wt. % propylene and between 0.1 and 50 wt. % propane.

52. The method of claim 51, wherein the portion of the propylene containing product stream introduced to the polypropylene reaction unit comprises at least 75 wt. % propylene and between 0.3 and 25 wt. % propane.

53. The method of claim 52, wherein the portion of the propylene containing product stream introduced to the polypropylene reaction unit comprises at least 90 wt. % propylene and between 0.5 and 10 wt. % propane.

54. The method of claim 45, wherein the propylene introduced into the polypropylene reaction unit has a hydrogen sulfide content of not greater than 10 ppm wt., a carbonyl sulfide content of not greater than 10 ppm wt., and an arsine content of not greater than 10 ppm wt.

55. The method of claim 45, wherein the propylene introduced into the polypropylene reactor is separated from the propylene containing product stream without subsequent removal of propane from propylene.

56. The method of claim 45, wherein the vent stream comprises propylene and propane.

* * * * *